US00PP34054P3

(12) United States Plant Patent
Post

(10) Patent No.: US PP34,054 P3
(45) Date of Patent: Mar. 22, 2022

(54) ***CHRYSANTHEMUM* PLANT NAMED 'DLFABB13'**

(50) Latin Name: ***Chrysanthemum* x *morifolium***
Varietal Denomination: DLFABB13

(71) Applicant: Arie Gerard Post, Delft (NL)

(72) Inventor: Arie Gerard Post, Delft (NL)

(73) Assignee: Deliflor Royalties B.V., Maasdijk (NL)

( * ) Notice: Subject to any disclaimer, the term of this patent is extended or adjusted under 35 U.S.C. 154(b) by 0 days.

(21) Appl. No.: 17/089,688

(22) Filed: Nov. 4, 2020

(65) Prior Publication Data

US 2021/0136981 P1 May 6, 2021

Related U.S. Application Data

(60) Provisional application No. 62/973,983, filed on Nov. 5, 2019.

(51) Int. Cl.
*A01H 5/02* (2018.01)
*A01H 6/14* (2018.01)

(52) U.S. Cl.
USPC ..... Plt./287
CPC ..... *A01H 6/1424* (2018.05)

(58) Field of Classification Search
USPC ..... Plt./287, 289
CPC ... A01H 5/02; A01H 5/00; A01H 6/14; A01H 6/1424
See application file for complete search history.

(56) References Cited

PUBLICATIONS

Deliflor Chrysanten 2020 Catalogue *Chrysanthemums*, retrieved on May 5, 2021, retrieved from the Internet at https://deliflor.blob.core.windows.net/website/UploadBestanden/Handelscatalogus-mrt-2020.pdf, cover page, pp. 2-3, 15. (Year: 2020).*

Floral Daily 2019 Deliflor introduces Abbey Yellow, retrieved on May 5, 2021, retrieved from the Internet at https://www.floraldaily.com/article/9106464/deliflor-introduces-abbey-yellow/, one page. (Year: 2019).*

* cited by examiner

*Primary Examiner* — June Hwu
(74) *Attorney, Agent, or Firm* — C. Anne Whealy

(57) ABSTRACT

A new and distinct cultivar of *Chrysanthemum* plant named 'DLFABB13', characterized by its upright plant habit; vigorous growth habit and rapid growth rate; dark green-colored leaves; uniform and freely flowering habit; strong upright flowering stems with numerous inflorescences; decorative-type inflorescences with bright yellow-colored ray florets that when developing are distally greyed red in color giving a bi-colored appearance to the inflorescences; relative tolerance to high production temperatures; resistance to *Fusarium* Wilt and White Rust; and good postproduction longevity.

2 Drawing Sheets

Botanical designation: *Chrysanthemum* X *morifolium*.
Cultivar denomination: 'DLFABB13'.

CROSS-REFERENCED TO CLOSELY-RELATED APPLICATIONS

Title: Varieties of *Chrysanthemum* Plants
Inventor/Applicant: Arie Gerard Post
Filed: Nov. 5, 2019
Ser. No. 62/973,983
Inventor/Applicant hereby claim the benefit of this provisional U.S. Patent Application.

STATEMENT REGARDING PRIOR DISCLOSURES BY INVENTOR/APPLICANT & ASSIGNEE

A Japanese Plant Breeder's Rights application for the instant plant was filed by the Assignee, Deliflor Royalties B.V. of Maasdijk, The Netherlands on Jul. 10, 2019, application number 34027. Additionally, an European Community Plant Breeder's Rights application for the instant plant was filed by the Assignee, Deliflor Royalties B.V. of Maasdijk, The Netherlands on Jul. 29, 2019, application number 2019/1837. Foreign priority is not claimed to these applications.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Chrysanthemum* plant, botanically known as *Chrysanthemum* x *morifolium*, typically grown as a cut flower *Chrysanthemum* and hereinafter referred to by the name 'DLFABB13'.

The new *Chrysanthemum* plant is a product of a planned breeding program conducted by the Inventor in Maasdijk, The Netherlands. The objective of the breeding program is to create new cut flower *Chrysanthemum* plants with numerous attractive inflorescences.

The new *Chrysanthemum* plant is a naturally-occurring whole plant mutation of *Chrysanthemum* x *morifolium* 'DLFABB12', disclosed in U.S. Plant Pat. No. 32,006. The new *Chrysanthemum* plant was discovered and selected as a single flowering plant from within a population of plants of 'DLFABB12' in a controlled greenhouse environment in Maasdijk, The Netherlands in January, 2018.

Asexual reproduction of the new *Chrysanthemum* plant by vegetative terminal cuttings since January, 2018 has shown that the unique features of this new *Chrysanthemum* plant are stable and reproduced true to type in successive generations of asexual reproduction.

SUMMARY OF THE INVENTION

Plants of the new *Chrysanthemum* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'DLFABB13'. These characteristics in combination distinguish 'DLFABB13' as a new and distinct *Chrysanthemum* plant:

1. Upright plant habit.
2. Vigorous growth habit and rapid growth rate.
3. Dark green-colored leaves.
4. Uniform and freely flowering habit.
5. Strong upright flowering stems with numerous inflorescences.
6. Decorative-type inflorescences with bright yellow-colored ray florets that when developing are distally greyed red in color giving a bi-colored appearance to the inflorescences.
7. Relatively tolerant to high production temperatures.
8. Resistant to *Fusarium* Wilt and White Rust.
9. Good postproduction longevity.

Plants of the new *Chrysanthemum* differ from plants of the mutation parent, 'DLFABB12', in ray floret color as plants of the new *Chrysanthemum* have bright yellow-colored ray florets that when developing are distally greyed red in color whereas ray florets of 'DLFABB12' are red purple to purple and white bi-colored.

Plants of the new *Chrysanthemum* can be compared to plants of *Chrysanthemum* X *morifolium* 'Delipinkyrock', not patented. In side-by-side comparisons, plants of the new *Chrysanthemum* differ primarily from plants of 'Delipinkyrock' in ray floret color as plants of the new *Chrysanthemum* have bright yellow-colored ray florets that when developing are distally greyed red in color whereas ray florets of 'Delipinkyrock' are light red purple in color.

BRIEF DESCRIPTION OF THE PHOTOGRAPHS

The accompanying photographs illustrate the overall appearance of the new *Chrysanthemum* plant showing the colors as true as it is reasonably possible to obtain in colored reproductions of this type.

The photograph on the first sheet comprises a side perspective view of a typical flowering stem of 'DLFABB13' grown as a spray-type cut flower.

The photograph on the second sheet is a close-up view of upper (top of the photographic sheet) and lower (bottom of the photographic sheet) surfaces of typical leaves (left) and inflorescences (right).

DETAILED BOTANICAL DESCRIPTION

The aforementioned photographs and following observations and measurements describe plants grown during the late spring in ground beds in a glass-covered greenhouse in Maasdijk, The Netherlands and under cultural practices typical of commercial cut *Chrysanthemum* production. Plants were initially given long day/short night treatments followed by short day/long night treatments to induce flower initiation and development. During the production of the plants, day temperatures ranged from 18° C. to 25° C., night temperatures ranged from 20° C. to 22° C. and light levels averaged 8 klux. Plants were grown as single-stem spray-type plants and were nine weeks old when the photographs and the description were taken. In the following description, color references are made to The Royal Horticultural Society Colour Chart, 2015 Edition, except where general terms of ordinary dictionary significance are used.

Botanical classification: *Chrysanthemum* X *morifolium* 'DLFABB13 '.

Parentage: Naturally-occurring whole plant mutation of *Chrysanthemum* x *morifolium* 'DLFABB12', disclosed in U.S. Plant Pat. No. 32,006.

Propagation:

*Type*.—Terminal vegetative cuttings.

*Time to initiate roots, summer*.—About four days at temperatures about 20° C.

*Time to initiate roots, winter*.—About six days at temperatures about 20° C.

*Time to produce a rooted young plant, summer*.—About 13 days at temperatures about 20° C.

*Time to produce a rooted young plant, winter*.—About 15 days at temperatures about 20° C.

*Root description*.—Fine, fibrous; typically light brown in color, actual color of the roots is dependent on substrate composition, water quality, fertilizers, substrate temperature and physiological age of roots.

*Rooting habit*.—Freely branching, medium density.

Plant description:

*Plant and growth habit*.—Herbaceous decorative-type cut flower that is typically grown as a single stem spray-type; upright plant habit; vigorous growth habit and rapid growth rate.

*Plant height, soil level to top of foliar plane*.—About 78.9 cm.

*Plant height, soil level to top of inflorescence plane*.—About 83.7 cm.

*Plant (spray) diameter*.—About 20 cm.

*Flowering stem length*.—About 77.9 cm.

*Flowering stem diameter*.—About 7.5 mm.

*Flowering stem internode length*.—About 2.5 cm.

*Flowering stem strength*.—Strong.

*Flowering stem aspect*.—Erect.

*Flowering stem texture and luster*.—Densely pubescent; slightly glossy.

*Flowering stem color, developing*.—Close to 143B to 143C.

*Flowering stem color, developed*.—Close to 146A to 146B.

*Leaf description*.—Arrangement: Alternate; simple. Length: About 12.3 cm. Width: About 6.8 cm. Shape: Oblong to broadly oblong. Apex: Abruptly acute. Base: Attenuate. Margin: Palmately lobed, coarsely crenate to dentate; sinuses convergent and medium to deep in depth. Texture and luster, upper surface: Moderately to densely pubescent, not rugose; moderately velvety; very slightly glossy. Texture and luster, lower surface: Moderately to densely pubescent, prominent venation; slightly velvety; very slightly glossy. Venation pattern: Pinnate, reticulate. Color: Developing leaves, upper surface: Close 137A. Developing leaves, lower surface: Close to between 138A and 147B. Fully developed leaves, upper surface: Slightly darker than close to between NN137A and 147A; venation, close to 147C. Fully developed leaves, lower surface: Close to 147B; venation, close to 146D. Petioles: Length: About 1.8 cm. Diameter: About 2 mm by 3 mm. Strength: Moderately strong. Texture and luster, upper and lower surfaces: Densely pubescent; slightly glossy. Color, upper surface: Close to 146B; edges, close to 141A. Color, lower surface: Close to 146C; edges, close to 143B. Stipules: Quantity and appearance: Two leafy stipules, opposite, at the petiole attachment to the stem. Length: About 9 mm. Width: About 9 mm. Shape: Broadly obovate to reniform and deeply incised to cleft. Texture and luster, upper surface: Moderately to densely pubescent, not rugose; moderately velvety; very slightly glossy. Texture and luster, lower surface: Moderately to densely pubescent, prominent venation; slightly velvety; very slightly glossy. Color, upper surface: Slightly darker than close to between NN137A and 147A. Color, lower surface: Close to 147B.

Inflorescence description:

*Appearance*.—Decorative-type inflorescence form with obovate to oblanceolate-shaped ray florets and tubular disc florets (if present); inflorescences borne perpendicular to peduncles and face mostly upright to slightly outwardly; ray and disc florets develop acropetally on a capitulum.

*Fragrance*.—Moderately fragrant; typical of *Chrysanthemums*.

*Flowering response*.—Under natural conditions, plant flower in the autumn/winter in the Northern Hemisphere; at other times of the year, inflorescence initiation and development can be induced under short day/long night conditions (at least 13.5 hours of darkness); uniform flowering habit and short response time, plants exposed to two weeks of long day/short night conditions after planting followed by photoinductive short day/long night conditions flower about 51 days later when grown as a spray-type.

*Postproduction longevity*.—Good postproduction longevity; in an interior environment, inflorescences and foliage will maintain good color and substance for about two weeks; inflorescences persistent.

*Quantity of inflorescences*.—Freely flowering habit; when grown as a spray-type, about 18 inflorescences develop per flowering stem.

*Inflorescence size*.—Diameter: About 5.5 cm. Depth (height): About 2.7 cm. Disc diameter: If present, about 2 mm; inconspicuous.

*Receptacles*.—Height: About 6 mm. Diameter: About 8 mm. Shape: Flattened globular. Color: Close to 145B to 145C.

*Inflorescence buds*.—Height: About 9 mm. Diameter: About 1.5 cm. Shape: Flattened globular. Texture and luster: Distally, smooth and glabrous; proximally, moderately pubescent; slightly glossy. Color: Close to 137A to 137B and 138A to 138B; immature ray florets, close to 22B and distally, close to darker than 178A to 178B.

*Ray florets*.—Quantity and arrangement: About 300 arranged in about ten whorls. Length: About 1.9 cm; varying between 1 cm and 2.5 cm. Width: About 8 mm; varying between 0.3 cm and 1.1 cm. Shape: Obovate to oblanceolate; moderately to strongly concave and moderately carinate. Apex: Broadly and bluntly acute or shallowly emarginate and shallowly praemorse. Base: Attenuate. Margin: Entire; not undulate. Aspect: Initially upright to about 45° from vertical. Texture and luster, upper surface: Smooth, glabrous; moderately velvety; matte. Texture and luster, lower surface: Smooth, glabrous; slightly velvety; slightly glossy. Color: When opening, upper surface: Close to 7B to 7C; distally, close to 178A. When opening, lower surface: Close to 8A to 8B; distally, close to 178A to 178B. Fully opened, upper and lower surfaces: Close to 4B to 4C; at the apex, faintly tinged with close to 179C; venation, similar to lamina colors; color becoming closer to 4B to 4C with subsequent development.

*Disc florets*.—Quantity and arrangement: If present, one or two at the center of the receptacle; disc florets inconspicuous. Length: About 5 mm. Diameter: About 1 mm. Shape: Lower 80% fused into a tube; upper 20% free. Apex: Narrowly acute. Margin, free-part: Entire. Texture and luster, inner and outer surfaces: Smooth, glabrous; glossy. Color, when opening, inner and outer surfaces: Distally, close to 154D; at the apex, close to 154B; and proximally, close to 145D. Color, fully opened, inner and outer surfaces: Distally, close to 154D; at the apex, close to 154C; and proximally, close to 145D.

*Involucral bracts*.—Quantity and arrangement: About 26 arranged in about two whorls. Length: About 1 cm. Width: About 4 mm. Shape: Narrowly ovate. Apex: Obtuse. Base: Cuneate. Margin: Entire. Texture and luster, upper surface: Smooth, glabrous; glossy. Texture and luster, lower surface: Moderately pubescent; matte. Color, upper surface: Close to 144A; margins, translucent and close to 192D and N199A. Color, lower surface: Close to 137A, 137B and 138A; margins, translucent and close to 192D and N199A.

*Peduncles*.—Length, terminal peduncle: About 5.8 cm. Diameter, terminal peduncle: About 3.5 mm. Length, third peduncle: About 9.4 cm. Diameter, third peduncle: About 2.5 mm. Strength: Strong. Aspect, terminal peduncle: Mostly upright. Aspect, third peduncle: About 30° from the flowering stem axis. Texture and luster: Densely pubescent; moderately glossy. Color: Close to 138B; venation, close to 137B.

*Reproductive organs*.—Androecium: Present on disc florets only. Quantity: About five per floret. Filament length: About 2 mm. Filament color: Close to 145C to 145D. Anther size: About 0.5 mm by 1.75 mm. Anther shape: Narrowly oblong. Anther color: Close to 14A. Pollen amount: Moderate. Pollen color: Close to 17A. Gynoecium: Present on both ray and disc florets. Quantity: One per floret. Pistil length: About 1.1 cm. Style length: About 1 cm. Style color: Close to 145C. Stigma diameter: About 1 mm. Stigma shape: Cleft, decurrent. Stigma color: Close to 5A. Ovary color: Close to 157D.

*Seeds and fruits*.—To date, seed and fruit production have not been observed on plants of the new *Chrysanthemum*.

Pathogen & pest resistance: Plants of the new *Chrysanthemum* have been observed to be resistant to *Fusarium* Wilt (*Fusarium oxysporum* spp. *chrysanthemi* (FoNL1)) and White Rust (*Puccinia horiana* (PhNL1)). To date, plants of the new *Chrysanthemum* have not been observed to be resistant or tolerant to pests and other pathogens common to *Chrysanthemum* plants grown under commercial conditions.

Temperature tolerance: Plants of the new *Chrysanthemum* have been observed to tolerate temperatures ranging from about −12° C. to 35° C. and to be suitable for USDA Hardiness Zones 8 to 10.

It is claimed:

1. A new and distinct *Chrysanthemum* plant named 'DLFABB13' as illustrated and described.

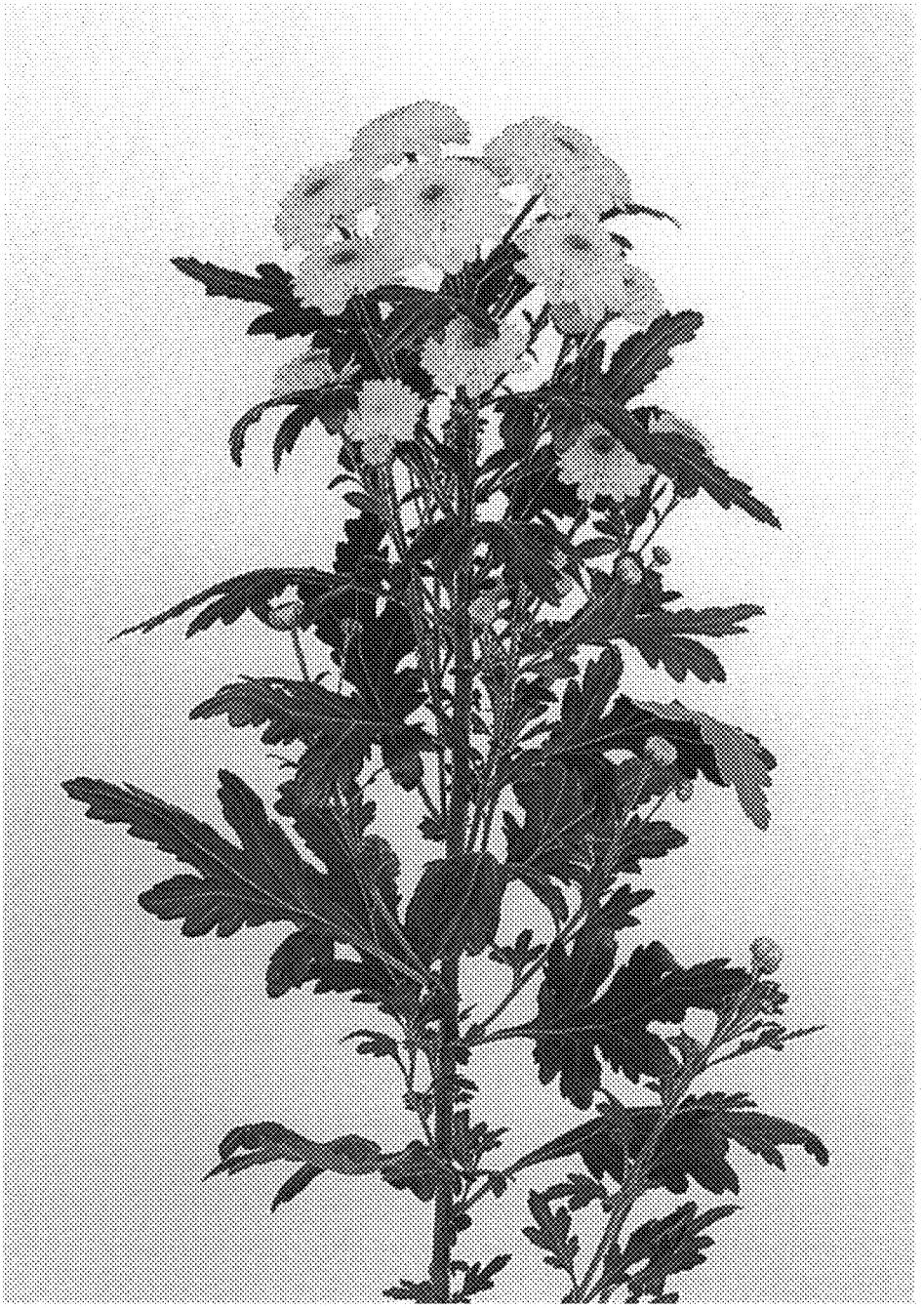

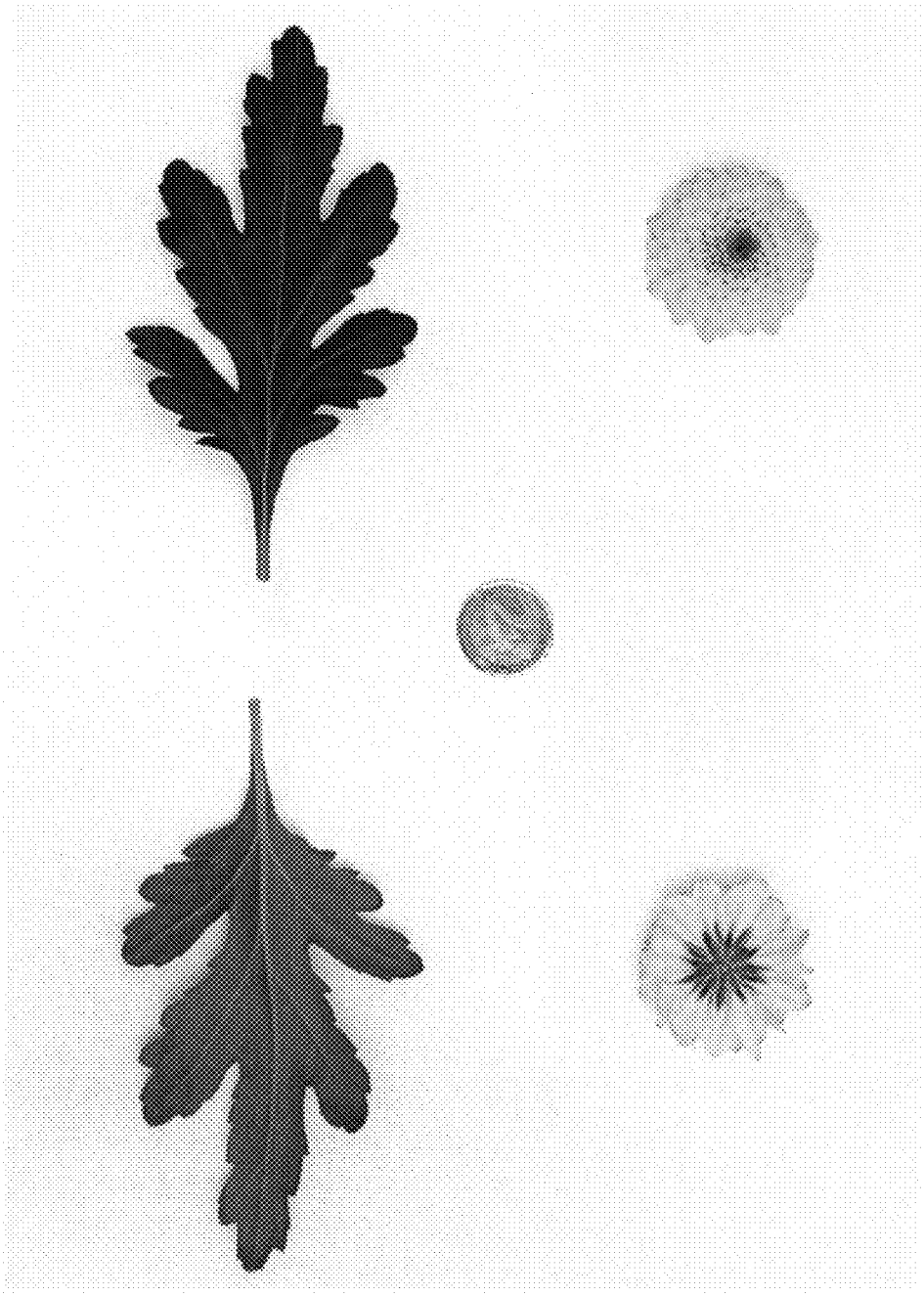

* * * * *